United States Patent
Wang et al.

(10) Patent No.: US 11,813,020 B2
(45) Date of Patent: *Nov. 14, 2023

(54) CAUTERIZATION DEVICES, METHODS, AND SYSTEMS

(71) Applicant: Boston Scientific Scimed, Inc., Maple Grove, MN (US)

(72) Inventors: Hui Wang, Fremont, CA (US); Wen-Jui Ray Chia, Sunnyvale, CA (US); Rongwei Jason Xuan, Fremont, CA (US); Jian James Zhang, Santa Clara, CA (US); Aditi Ray, Folsom, CA (US); Honggang Yu, San Jose, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 296 days.

This patent is subject to a terminal disclaimer.

(21) Appl. No.: 16/778,069

(22) Filed: Jan. 31, 2020

(65) Prior Publication Data

US 2020/0163716 A1 May 28, 2020

Related U.S. Application Data

(63) Continuation of application No. 16/185,931, filed on Nov. 9, 2018, now Pat. No. 10,582,967, which is a continuation of application No. 15/209,277, filed on Jul. 13, 2016, now Pat. No. 10,149,717.

(60) Provisional application No. 62/195,375, filed on Jul. 22, 2015, provisional application No. 62/192,098, filed on Jul. 14, 2015.

(51) Int. Cl.
*A61B 18/22* (2006.01)
*A61B 18/28* (2006.01)
(Continued)

(52) U.S. Cl.
CPC ............. *A61B 18/22* (2013.01); *A61B 18/28* (2013.01); *A61B 18/1482* (2013.01);
(Continued)

(58) Field of Classification Search
CPC ... A61B 18/04; A61B 18/082; A61B 18/1482; A61B 18/22; A61B 18/28;
(Continued)

(56) References Cited

U.S. PATENT DOCUMENTS

| | | | |
|---|---|---|---|
| 4,848,339 A | | 7/1989 | Rink et al. |
| 5,242,437 A | * | 9/1993 | Everett .................. A61B 18/24 606/15 |
| 7,869,016 B2 | | 1/2011 | Mitchell et al. |
| 8,858,542 B2 | | 10/2014 | Peng et al. |

(Continued)

FOREIGN PATENT DOCUMENTS

| | | |
|---|---|---|
| CN | 101951851 A | 1/2011 |
| CN | 101965159 A | 2/2011 |

(Continued)

OTHER PUBLICATIONS

International Search Report and Written Opinion in corresponding International Application No. PCT/US2016/042072 dated Oct. 18, 2016, 11 pages.

*Primary Examiner* — Scott Luan

(74) *Attorney, Agent, or Firm* — Seager, Tufte & Wickhem, LLP

(57) ABSTRACT

Aspects of this disclosure pertain to a device with an elongated body having a distal end. The distal end may comprise a port that permits discharge of a laser energy towards a tissue from an optical fiber located in the distal end. An exterior surface of the distal end may include a cauterization portion that permits discharge of a cauterization energy towards the tissue. In some aspects, the device includes an insulative portion that attaches the distal end to the elongated body and limits energy transfer therebetween. Related systems and methods are also disclosed.

20 Claims, 7 Drawing Sheets

(51) Int. Cl.
   *A61B 18/14*    (2006.01)
   *A61B 18/00*    (2006.01)
   *A61B 18/20*    (2006.01)

(52) U.S. Cl.
   CPC ........... *A61B 2018/00101* (2013.01); *A61B 2018/00577* (2013.01); *A61B 2018/00595* (2013.01); *A61B 2018/2065* (2013.01); *A61B 2018/2211* (2013.01); *A61B 2018/2272* (2013.01); *A61B 2018/2285* (2017.05)

(58) Field of Classification Search
   CPC ........... A61B 2018/00101; A61B 2018/00595; A61B 2018/2065; A61B 2018/2272
   See application file for complete search history.

(56) References Cited

U.S. PATENT DOCUMENTS

| | | | |
|---|---|---|---|
| 2001/0025190 A1 | 9/2001 | Weber et al. | |
| 2007/0100405 A1* | 5/2007 | Thompson | A61B 18/1492 607/113 |
| 2009/0306637 A1* | 12/2009 | Esch | A61B 18/24 606/15 |
| 2012/0022512 A1 | 1/2012 | Vaynberg | |
| 2014/0276790 A1 | 9/2014 | Raybin et al. | |
| 2015/0011985 A1 | 1/2015 | Peng et al. | |

FOREIGN PATENT DOCUMENTS

| | | |
|---|---|---|
| CN | 103997981 A | 8/2014 |
| JP | H02-277450 A | 11/1990 |
| WO | WO 2015/061201 | 4/2015 |

\* cited by examiner

CAUTERIZATION DEVICES, METHODS, AND SYSTEMS

CROSS-REFERENCE TO RELATED APPLICATIONS

This patent application is a continuation of U.S. patent application Ser. No. 16/185,931, filed Nov. 9, 2018, which is a continuation of U.S. patent application Ser. No. 15/209,277, filed Jul. 13, 2016, now U.S. Pat. No. 10,149,717, which claims the benefit of priority under 35 U.S.C. § 119 to U.S. Provisional Patent Application No. 62/192,098, filed Jul. 14, 2015, and U.S. Provisional Patent Application No. 62/195,375, filed Jul. 22, 2015, the entireties of each of the aforementioned applications is herein incorporated by reference.

TECHNICAL FIELD

Aspects of this disclosure relate to laser devices including, for example, laser systems, laser bars and laser modules comprising laser diodes, and methods of using the laser devices. Some aspects relate particularly to cauterization devices, methods, and systems, such as those including laser devices.

BACKGROUND

Lasers have been increasingly adopted as medical surgical tools. Optical fibers have are normally used to deliver laser energy during, for example, a laser surgery. As compared to traditional surgical tools, laser surgery can reduce bleeding, pain and infection. Additionally, patients often have less hospitalization time after laser surgery.

Laser energy may be less efficient than conventional electrical heating devices at stopping bleeding (coagulation), such as bleeding from incised blood vessels. Therefore, many surgeons will use a laser tool in some procedural steps, and a separate cauterization tool for other steps. Using multiple tools may complicate certain procedures, such as those performed in a relatively confined portion of the body, like an interior portion of a kidney. These complications may increase operating time and, thus, the cost of such procedures.

SUMMARY

Aspects of the present disclosure relate to cauterization devices, methods, and systems. Numerous aspects of the present disclosure are now described.

One aspect of this disclosure is a device with an elongated body having a distal end. The distal end may comprise: a port that permits discharge of a laser energy towards a tissue from an optical fiber located in the distal end; an exterior surface including a cauterization portion that permits discharge of a cauterization energy towards the tissue; and an insulative portion that attaches the distal end to the elongated body and limits energy transfer therebetween.

According to this aspect, the port of an exemplary device may be adjacent the cauterization portion. The distal end may have a longitudinal axis, and the port may extend through the cauterization portion along an axis transverse to the longitudinal axis. The cauterization portion may comprise the entire exterior surface of the distal end. In some aspects, the cauterization energy may be an electrical energy, and the cauterization portion may include an electrical conductor extending proximally through, for example, the insulative portion and the elongated body for connection to a source of electrical energy. In other instances, the cauterization energy may be a thermal energy, and, for example, the laser energy may be discharged towards the tissue at a first power level to perform a treatment, and towards the cauterization portion at a second power level to generate the thermal energy. The optical fiber may include a first optical fiber that discharges a first laser energy toward the tissue, and a second optical fiber that discharges a second laser energy towards the cauterization portion to generate the thermal energy. These first and second laser energies may have different power levels and/or wavelengths.

Another aspect of the present disclosure is a system. An exemplary system may comprise: an elongated body including a distal end and at least one lumen; an optical fiber extending through the at least one lumen for discharge of a laser energy; a port on the distal end for discharge of the laser energy towards a tissue; a cauterization portion on the distal end for discharge of a cauterization energy toward the tissue; and an insulative portion that attaches the distal end to the elongated body and limits energy transfer therebetween.

According to this aspect, the distal end of the elongated body in an exemplary system may be removably attached to the elongated body. The port may extend through the cauterization portion. In some aspects, the cauterization energy may be an electrical energy, and the cauterization portion may include an electrical conductor, which may extend proximally through the insulative portion and/or the elongated body for connection to a source of electrical energy. In other aspects, the cauterization energy may be a thermal energy, and the laser energy may be dischargeable towards the cauterization portion to generate the thermal energy. For example, the optical fiber may be mounted in the elongated element for movement between a first position, wherein the laser energy is discharged through the port towards the tissue, to a second position, wherein the laser energy is discharged towards an interior surface of cauterization portion. The laser energy may be discharged towards the tissue at a first power level, and towards the interior surface of the cauterization portion at a second power level greater than the first power level. The laser energy also may be discharged towards the tissue at a first wavelength, and towards the interior surface of the cauterization portion at a second wavelength different from the first wavelength.

Yet another aspect of the present disclosure is a method. For example, this method may comprise: positioning a distal end of a device adjacent a tissue, the distal end including a port and a cauterization portion; aligning the port with a treatment area of the tissue; discharging a laser energy through the port and towards the treatment area; positioning the cauterization portion adjacent the treatment area; and discharging a cauterization energy through the cauterization portion and towards the treatment area.

According to this aspect, the method may further comprise attaching the distal end to an elongated body of device so as to limit energy transfer between the distal end and the elongated body. In some aspects, the cauterization energy may be an electrical energy, and discharging the cauterization energy may comprise activing a source of electrical energy. In other aspects, the cauterization energy may include a thermal energy, and discharging the cauterization energy may comprise discharging the laser energy towards the cauterization portion to generate the thermal energy. The distal end may be attached to the elongated body, and the laser energy may be discharged through an optical fiber mounted in a lumen of the elongated body. In which case, the method may further comprise: moving the optical fiber to a first position in the lumen before discharging the laser energy through the port; and moving the optical fiber to a second position in the lumen before discharging the laser energy towards an interior surface of the cauterization portion.

It may be understood that both the foregoing summary and the following detailed descriptions are exemplary and explanatory only, neither being restrictive of the inventions claimed below.

BRIEF DESCRIPTION OF THE DRAWINGS

The accompanying drawings are incorporated in and constitute a part of this disclosure. These drawings illustrate aspects that, together with the written descriptions, serve to explain the principles of this disclosure.

FIGS. 5A and 58 are simplified side cross-sectional views of a distal end of an exemplary energy delivery device in accordance with aspects of this disclosure respectively performing exemplary laser and cauterization operations.

DETAILED DESCRIPTION

Figure 1:
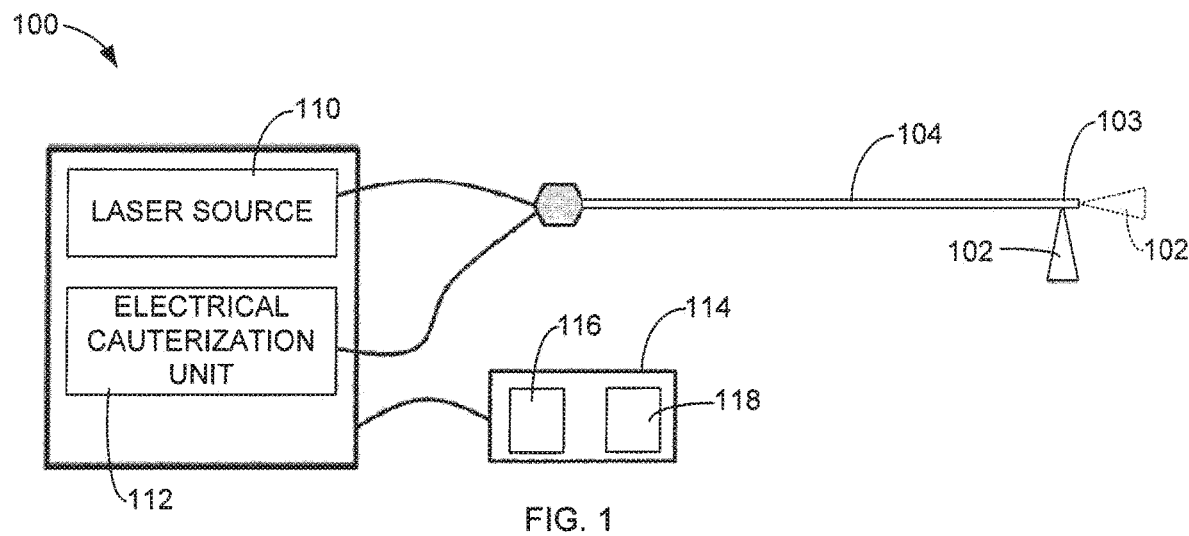
FIG. 1 is a simplified diagram of an exemplary medical laser system with electrical cauterization in accordance with aspects of this disclosure.

Aspects of this disclosure are described more fully hereinafter with reference to the accompanying drawings. Elements that are identified using the same or similar reference characters refer to the same or similar elements. The various aspects of this disclosure may, however, be embodied in many different forms and should not be construed as limited to the aspects set forth herein. Rather, these aspects are provided so that this disclosure will be thorough and complete, and will convey the scope of this disclosure to those skilled in the art.

Specific details are given in the following description to provide a thorough understanding of the aspects. However, it is understood by those of ordinary skill in the art that the aspects may be practiced without these specific details. For example, circuits, systems, networks, processes, frames, supports, connectors, motors, processors, and other components may not be shown, or shown in block diagram form in order to not obscure the aspects in unnecessary detail.

The terminology used herein is for the purpose of describing particular aspects only and is not intended to be limiting of this disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

It will be understood that when an element is referred to as being "connected" or "coupled" to another element, it can be directly connected or coupled to the other element or intervening elements may be present. In contrast, if an element is referred to as being "directly connected" or "directly coupled" to another element, there are no intervening elements present.

It will be understood that, although the terms first, second, etc. may be used herein to describe various elements, these elements should not be limited by these terms. These terms are only used to distinguish one element from another. Thus, a first element could be termed a second element without departing from the teachings of the present disclosure.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

As will further be appreciated by one of skill in the art, the present disclosure may be embodied as methods, systems, devices, and/or computer program products, for example. Accordingly, the present disclosure may take the form of an entirely hardware aspect, an entirely software aspect or an aspect combining software and hardware aspects. The computer program or software aspect of the present disclosure may comprise computer readable instructions or code stored in a computer readable medium or memory. Execution of the program instructions by one or more processors (e.g., central processing unit) results in the one or more processors performing one or more functions or method steps described herein. Any suitable patent subject matter eligible computer readable media or memory may be utilized including, for example, hard disks, CD-ROMs, optical storage devices, or magnetic storage devices. Such computer readable media or memory do not include transitory waves or signals.

The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following; an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

Aspects of this disclosure may also be described using flowchart illustrations and block diagrams. Although a flowchart may describe the operations as a sequential process, many of the operations can be performed in parallel or concurrently. In addition, the order of the operations may be re-arranged. A process is terminated when its operations are completed, but could have additional steps not included in a figure or described herein.

FIG. 1 is a simplified diagram of an exemplary system 100 configured to perform laser operations and electrical cauterization operations in accordance with aspects of this disclosure. The system 100 is generally configured to discharge laser energy 102 from a distal end 103 of an energy delivery device 104 for use in a medical laser operation, such as tissue cutting, ablation, vaporization, or other medical laser operation. Additionally, the system 100 is configured to perform an electrical cauterization operation at the distal end 103 of the energy delivery device 104.

The energy delivery device 104 may be supported in an endoscope or other suitable probe. Endoscopes can be used to provide imaging guidance and a flow of cooling liquid, in accordance with conventional practices.

In some aspects, the system 100 includes a laser source 110 and an electrical cauterization unit 112. The laser source 110 is configured to generate the laser energy 102 that is optically coupled to the energy delivery device 104 in accordance with conventional techniques. The electrical cauterization unit 112 is configured to generate electrical energy in the form of an electrical current that is coupled to the energy delivery device 104 through one or more electrical conductors.

In some aspects, the system 100 includes one or more input devices 114 that are used by the operator of the system 100 to control the delivery of the laser energy 102 and the electrical energy through the energy delivery device 104. In some aspects, the input device 114 includes at least one switch 116 for operating the laser source 110, and at least one switch 118 for operating the electrical cauterization unit 112. In some aspects, the switches 116 and 118 may be implemented using foot pedals, buttons, or other suitable input devices.

In some aspects, the laser source 110 and the electrical cauterization unit 112 are each standalone units. In some aspects, the laser source 110 and the electrical cauterization unit 112 are integrated into a single console, as illustrated in FIG. 1.

Figure 2A:
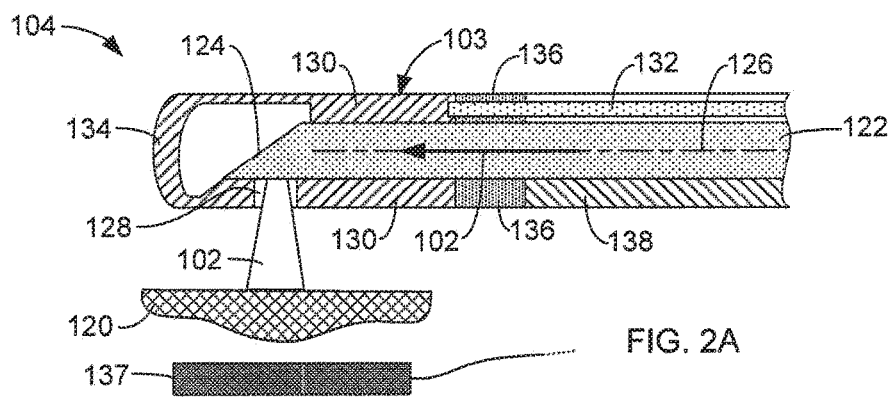
FIGS. 2A and 2B are simplified side cross-sectional views of a distal end of an exemplary energy delivery device in accordance with aspects of this disclosure respectively performing a laser operation and an electrical cauterization operation.
Figure 3A:
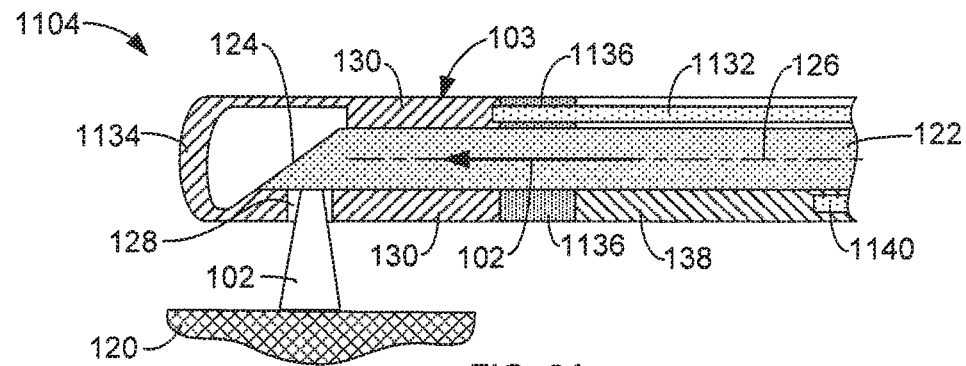
FIGS. 3A and 3B are simplified side cross-sectional views of a distal end of an exemplary energy delivery device in accordance with aspects of this disclosure respectively performing a laser operation and an electrical cauterization operation.
Figure 3B:
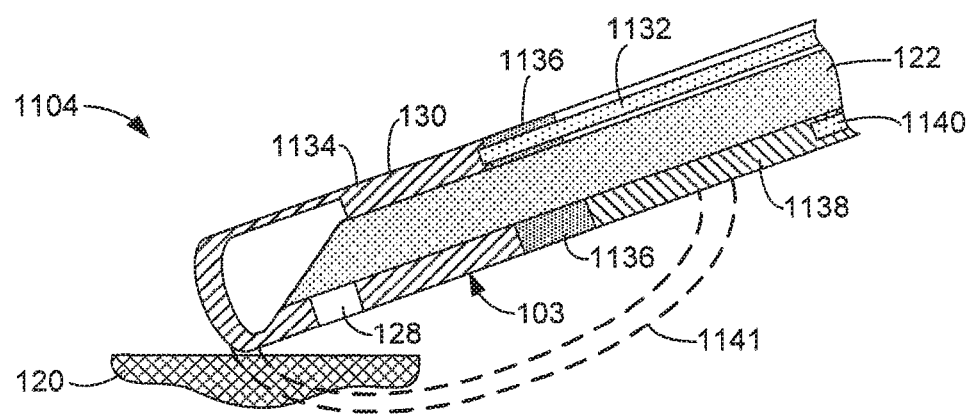

FIGS. 2A and 28 are simplified side cross-sectional views of the distal end 103 of an exemplary energy delivery device 104 in accordance with aspects of this disclosure respectfully performing a laser operation and an electrical cauterization operation on tissue 120. FIGS. 3A and 3B are simplified side cross-sectional views of the distal end 103 of an exemplary energy delivery device 1104 in accordance with aspects of this disclosure respectfully performing a laser operation and an electrical cauterization operation on tissue 120. In some aspects, the energy delivery device 104 includes an optical or laser fiber 122 that is configured to receive the laser energy 102 generated by the laser source 110 and transmit the laser energy 102 to the distal end 103 where it is discharged for performing the desired laser operation, as shown in FIGS. 2A and 3A. The optical or laser fiber 122 may take on various conventional forms. For example, the laser fiber 122 may have a side-fire configuration, in which a terminating end 124 has a beveled surface configured to reflect the laser energy 102 laterally relative to a longitudinal axis 126 and discharge the laser energy 102 through a side port 128 of the device 104 to the targeted tissue 120, as shown in FIGS. 2A and 3A. Alternatively, the laser fiber 122 may be configured to discharge the laser energy 102 along the longitudinal axis 126 of the laser fiber 122 at the terminating end and through a suitable port of the device 104 (end-fire configuration).

The electrical cauterization function of the energy delivery devices 104 and 1104 can be realized in a monopolar form or a bipolar form. In general, the energy delivery devices 104 and 1104 respectively include at least a first electrical conductor 132, 1132, which can be in the form of a metal wire, that receives electrical energy from the electrical cauterization unit 112 and delivers the electrical energy in the form of an electrical current to a cauterization portion 130 at the distal end 103 of the energy delivery devices 104 and 1104. In some aspects, the cauterization portion 130 includes an electrically conductive portion or element 134 (FIGS. 2A and 2B) or 1134 (FIGS. 3A and 38) that is supported at the distal end 103. In some aspects, the portions 134 and 1134 are in the form of a metal cap, as shown in FIGS. 2A and 3A. In some aspects, the electrically conductive portion 134 or 1134 includes the port 128, through which the laser energy 102 may be discharged, as shown in FIGS. 2A and 3A. In some aspects, the cauterization portion 130 includes an electrically insulative portion 136 (FIG. 2A) or 1136 (FIG. 3A) located toward the proximal end of the device 104 from the electrically conductive portion 134 or 1134, respectively. The electrically insulative portion 136 or 1136 operates to insulate the electrically conductive portion 134 or 1134 from components of the energy delivery device 104 or 1104, other than the conductor 132. In some aspects, the electrically insulative portion 136 or 1136 is formed of a polymer or ceramic material.

Figure 2B:
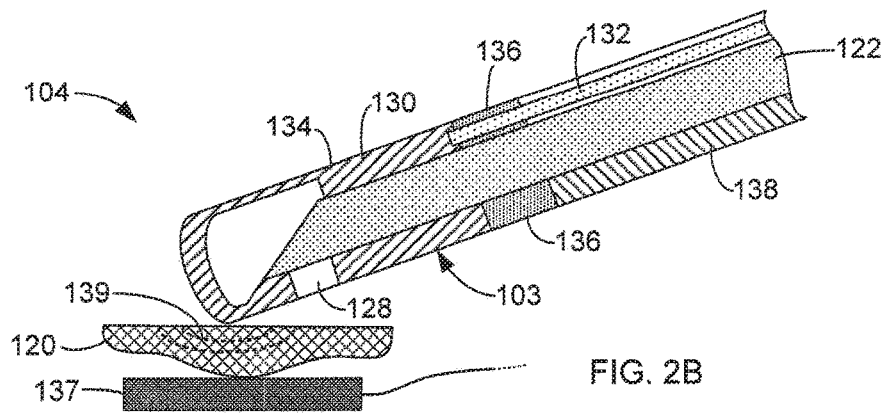

Depicted in FIGS. 2A and 28 is a monopolar aspect of this disclosure. In this aspect, the energy delivery device 104 includes a laser fiber 122 having a longitudinal axis 126, a cauterization portion 130 included on a distal portion of the laser fiber 122 and having an electrically conductive portion 134 and a side port 128, an electrical conductor 132 and an electrically insulative portion 136. As can be seen in FIGS. 2A and 28, the electrical conductor 132 connects to the cauterization portion 130 through the electrically insulative portion 136. In this monopolar aspect, a return pad 137 may be necessary to complete the electric circuit allowing current 139 to flow from the cauterization portion 130, through the tissue 120 and into the return pad 137 thereby cauterizing the tissue 120, as depicted in FIG. 2B.

In some aspects, as depicted in FIGS. 3A and 3B, the delivery device 1104 has a bipolar configuration, and includes a first electrically conductive element 1134 that is electrically coupled to a first electrical conductor 1132. In addition, the delivery device 1104 includes a second electrically conductive element 1138 that is electrically coupled to a second electrical conductor 1140. The first and second electrical conductors can be, for example, metal wire. In order to isolate the first electrically conductive element 1134 from the second electrically conductive element 1138, an electrically insulative, non-conductive material 1136 is included between the first electrically conductive element 1134 from the second electrically conductive element 1138. The non-conductive material 1136 can be, for example, a polymeric or ceramic material.

In use, electrical current 1141 delivered to the tissue 1120 through the first electrical conductor 1132, to the first electrically conductive element 1134, through the tissue 120, into the second electrically conductive element 1138, to the second electrical conductor 1140 and then back to the electrical cauterization unit 112. In some aspects, the first electrically conductive element 1134 is in the form of a cap that is glued or crimped to the electrically insulative portion 1136 or other component of the energy delivery device 1104.

During a laser operation, laser energy 102 is generated by the laser source 110 and delivered to a proximal end of the optical fiber 122. The laser energy is delivered through the optical fiber 122 to the distal end 103 of the energy delivery device 104 where it is discharged toward the targeted tissue 120 of the patient. The laser energy 102 may be discharged laterally (side-fire configuration) through a port 128 to the tissue 120, as shown in FIGS. 2A, 2B, 3A and 3B. Alternatively, the terminating distal end of the fiber 122 may be configured to discharge the laser energy 102 along the axis 126 of the fiber to the targeted tissue, as indicated in phantom lines in FIG. 1. The generation of the laser energy 102 by the laser source 110 may be controlled through a suitable input device 114 by the user of the system 100.

An electrical cauterization operation can be performed by enabling the electrical cauterization unit 112 to produce electrical energy, which is delivered to the distal end 103 of the energy delivery device 104, 1104 through the first electrical conductor 132, 1132. The generation of the electrical energy may be triggered using a suitable input device 114 by the user. The electrical energy in the form of an electrical current is conducted to the targeted tissue 120 through the electrically conductive portion 134 or first electrically conductive element 1134. In the monopolar aspect of FIGS. 2A and 2B, a return path for the electrical current 139 to the electrical cauterization unit 112 may be provided through the return pad 137 that is attached to the patient. In the bipolar aspect of FIGS. 3A and 3B, the electrical current 1141 may be returned to the electrical cauterization unit 112 through the second electrically conductive element 1138 and the second electrical conductor 1140. The delivery of the electrical current to the tissue 120 of the patient generates heat that cauterizes the tissue 120 to stop bleeding.

In general, such an electrical cauterization operation is performed after a laser operation in order to control bleeding in the patient. The input device 114 allows the user to quickly switch between the laser operation and the electrical cauterization operation as needed.

Figure 4:
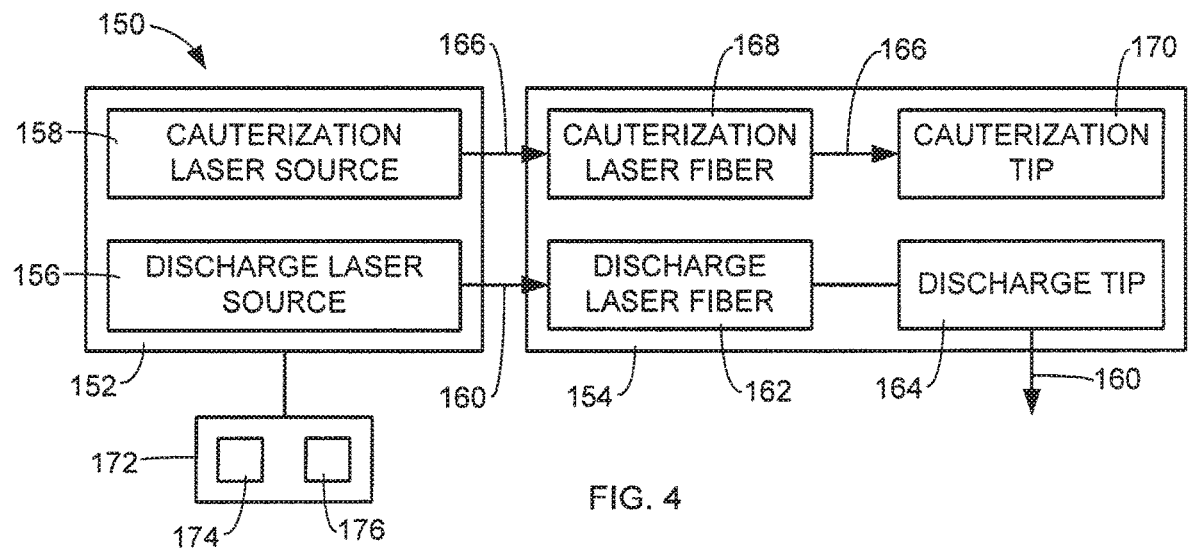
FIG. 4 is a simplified diagram of an exemplary medical laser system in accordance with aspects of this disclosure.

FIG. 4 is a simplified diagram of an exemplary system 150 that is configured to perform laser and cauterization operations according to another aspect of this disclosure. In some aspects, the cauterization operations are performed by conducting laser-generated heat to the targeted tissue.

In some aspects, the system 150 includes a laser source 152 and an energy delivery device 154. In some aspects, the laser source 152 includes a discharge laser source 156 and a cauterization laser source 158. The discharge laser source 156 is configured to generate laser energy 160 that is optically coupled to a discharge laser fiber 162. The discharge laser fiber 162 transmits the laser energy 160 to a discharge tip 164, which discharges the laser energy 160 toward targeted tissue 182 during a laser operation in order to perform a laser treatment such as, for example, vaporization, etc.

The cauterization laser source 158 is configured to generate laser energy 166 that is optically coupled to a cauterization laser fiber 168. The cauterization laser fiber 168 is configured to discharge the laser energy 166 to a cauterization tip 170 to heat the cauterization tip 170 and perform a cauterization operation (see FIG. 58). In general, the cauterization tip 170, heated in response to exposure to the laser energy 166, is placed in contact with targeted tissue 182 to heat and cauterize the tissue to stop bleeding.

In some aspects, the system 150 includes at least one input device 172 to control the discharge laser source 156 and the cauterization laser source 158. In some aspects, the input device 172 includes a switch 174 for activating and deactivating the discharge laser source 156, and a switch 176 for activating and deactivating the cauterization laser source 158. In some aspects, the switches 174 and 176 are in the form of foot pedals or other suitable input devices.

Figure 5A:
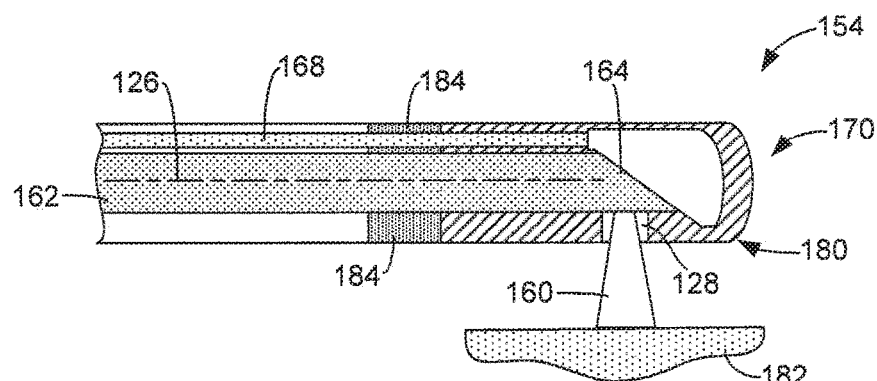
Figure 5B:
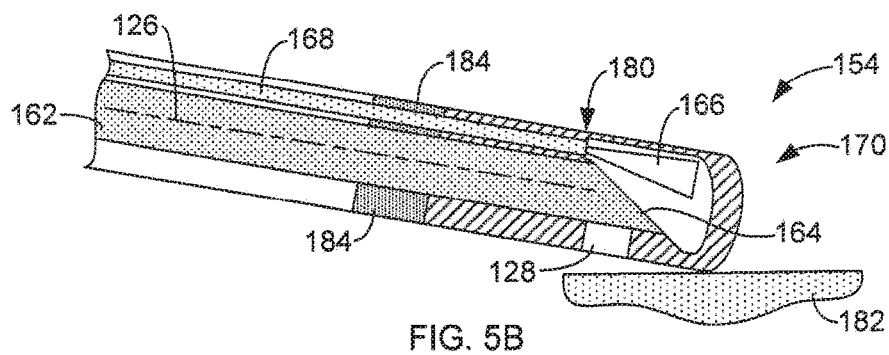

FIGS. 5A and 5B are simplified side cross-sectional views of a distal end 180 of an exemplary energy delivery device 154 in accordance with aspects of this disclosure performing an exemplary laser operation (FIG. 5A) and cauterization operation (FIG. 5B). In some aspects, the discharge laser fiber 162 has a proximal end that receives the laser energy 160 generated by the discharge laser source 156. The laser energy 160 is transmitted through the fiber 162 to the discharge tip 164 where it is discharged toward targeted tissue 182, as shown in FIG. 5A. The discharge laser fiber 162 may be formed in accordance with the aspects of the laser fiber 122 described above with regard to FIGS. 2 and 3. For example, the discharge laser fiber 162 may be configured to discharge the laser energy 160 laterally relative to a longitudinal axis 126 of the discharge laser fiber 162 (side-fire configuration), or the discharge laser fiber 162 may be configured to discharge the laser energy 160 along the longitudinal axis 126 (end-fire configuration). The discharge laser fiber 162 may also be configured to discharge the laser energy 160 in accordance with other conventional techniques. If necessary, the discharge laser energy 160 may be discharged through a port of the energy delivery device 154, such as port 128 shown in FIGS. 5A and 58.

In some aspects, the energy delivery device 154 includes the cauterization laser fiber 168 that receives the laser energy 166 generated by the cauterization laser source 158 and delivers the cauterization laser energy 166 to the cauterization tip 170. In some aspects, the cauterization tip 170 includes a thermally conductive element formed of a material that absorbs the cauterization laser energy 166 and is positioned to receive the cauterization laser energy 166 discharged from the cauterization laser fiber 168, as shown in FIG. 58. In some aspects, the cauterization tip 170 is in the form of a metal cap that is secured (e.g., crimped, glued, etc.) to the discharge laser fiber 162, the cauterization laser fiber 168, and/or other components of the energy delivery device 154, as shown in FIGS. 5A and 58.

In some aspects, the distal end of the cauterization laser fiber 168 through which the cauterization laser energy 166 is discharged is sufficiently spaced from the cauterization tip 170 to avoid damage due to the discharge of the laser energy 166 and the associated heating of the cauterization tip 170 responsive to the exposure to the cauterization laser energy 166. In some aspects, the energy delivery device 154 includes an insulative element 184 located on the proximal side of the cauterization tip 170 that is configured to insulate elements of the energy delivery device 154 from the heat generated at the distal end 180 due to the discharge of the cauterization laser energy 166. In some aspects, the insulative element 184 extends distally as illustrated in FIG. 5A to thermally insulate the cauterization laser fiber 168 and the discharge tip 164 from heat generated responsive to the discharge of the cauterization laser energy 166 from the cauterization laser fiber 168. In some aspects, the cauterization tip 170 is attached directly to the insulative element 182.

During a laser operation/treatment, a user triggers activation of the discharge laser source 156, such as by using the input device 172, to generate the discharge laser energy 160. The laser energy 160 is optically coupled to the discharge laser fiber 162, which delivers the laser energy 160 to the discharge tip 164 where it is discharged to targeted tissue 182 to perform the desired laser operation on the tissue 182. When the user wishes to cauterize tissue of the patient, such as due to bleeding after the performance of the laser operation, the discharge laser source 156 is deactivated, and the cauterization laser source 158 is activated by the user, such as through the input device 172. The cauterization laser energy 166 generated by the cauterization laser source 158 is delivered to the cauterization tip 170 through the cauterization laser fiber 168. Exposure of the cauterization tip 170 to the cauterization laser energy 166 quickly heats the cauterization tip 170. The tip 170 can then be brought into contact with the targeted tissue 182 to cauterize the tissue 182, as shown in FIG. 5B.

In some aspects, the laser energy 160 generated by the discharge laser source 156 includes relatively high power laser energy that is useful for tissue cutting, ablation, vaporization, or other medical laser operations/treatments. In some aspects, the laser energy 166 generated by the cauterization laser source 158 has a relatively low power compared to the laser energy 160, such as less than 10 watts. In some aspects, the cauterization tip 170 is heated to around 60-80° C. to perform the cauterization operation.

In some aspects, the wavelengths of the discharge laser energy 160 and the cauterization laser energy 166 are the same. In some aspects, the wavelengths of the discharge laser energy 160 and the cauterization laser energy 166 are different. For example, the wavelengths of the laser energy 160 and 166 may be the same but at different power levels. Furthermore, while the discharge laser energy 160 is selected to efficiently perform the desired laser operation, the cauterization laser energy 166 may be selected to efficiently heat the cauterization tip 170. Thus, in some aspects, the cauterization laser energy 166 has a wavelength that is adapted to efficiently heat the cauterization tip 170. Other factors for determining the wavelength and power levels of the laser energies 160 and 166 include the diameter of the discharge laser fiber 162 and the cauterization laser fiber 168, and the laser beam output quality from the laser sources 156 and 158, for example.

In some aspects, a single laser source is used to produce both the discharge laser energy 160 and the cauterization laser energy 166. In accordance with this aspect, suitable optics are used to selectively couple the laser energy outputs from the single laser source to either the discharge laser fiber 162 or the cauterization laser fiber 168. The settings of the single laser source may be adjusted to provide the desired energy/power levels and/or wavelengths of the laser energies 160 and 166.

Figure 6:
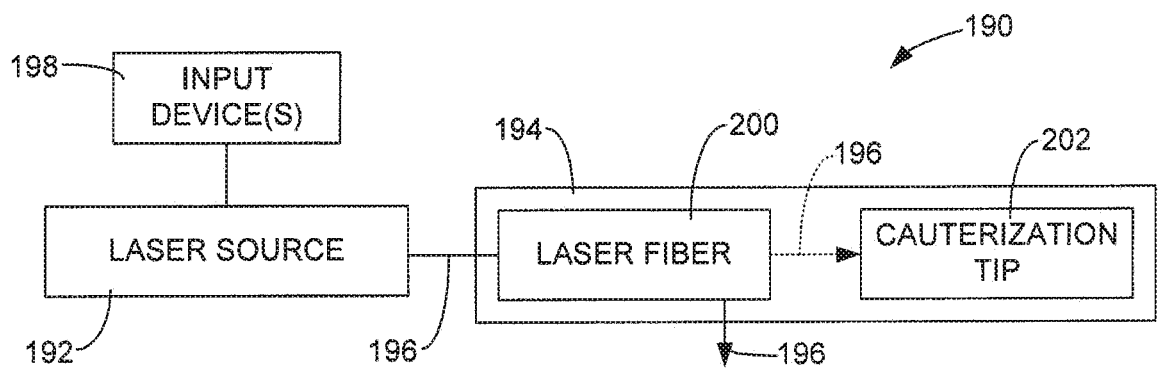
FIG. 6 is a simplified diagram of an exemplary medical laser system in accordance with aspects of this disclosure.

FIG. 6 is a simplified diagram of an exemplary medical laser system 190 in accordance with aspects of this disclosure. In some aspects, the system 190 includes a laser source 192 and an energy delivery device 194. In some aspects, the laser source 192 is configured to produce laser energy 196 for use in performing a medical laser operation, such as those described above. The laser source 192 may be configured to output the laser energy 196 at different wavelengths and power levels. In some aspects, the system 190 includes one or more input devices 198, through which a user controls the activation of the laser source 192 to generate the laser energy 196, adjust settings of the laser source 192 to control the wavelength and/or power level of the laser energy 196, and/or perform other functions. The input devices can be any of those previously disclosed and described.

In some aspects, the energy delivery device 194 includes a laser fiber 200 that is optically coupled to the laser energy 196 generated by the laser source 192. The laser fiber 200 is configured to discharge the laser energy 196 in a desired direction, such as laterally with respect to a longitudinal axis of the laser fiber 200 (side-fire configuration), or along the longitudinal axis of the laser fiber (end-fire configuration). In some aspects, the energy delivery device 194 is configured to perform a laser operation by directing the laser energy 196 toward targeted tissue of a patient. In some aspects, the energy delivery device 194 is configured to direct the laser energy 196 discharged from the laser fiber 200 to a cauterization tip 202. The exposure of the cauterization tip 202 to the laser energy 196 heats the cauterization tip 202, which can be used to perform a cauterization operation on the patient. In some aspects, the laser fiber 200 is moved relative to the cauterization tip 202 to expose the cauterization tip 202 to the laser energy 196. The laser fiber 200 may then be moved again relative to the cauterization tip 202 to discharge the laser energy 196 toward the targeted tissue to perform a laser operation on the tissue. In other aspects, the cauterization tip 202 is moved relative to the laser fiber 200 to switch between discharging laser energy 196 to targeted tissue and discharging laser energy 196 to the cauterization tip 202 to perform cauterization on targeted tissue.

Figure 7:
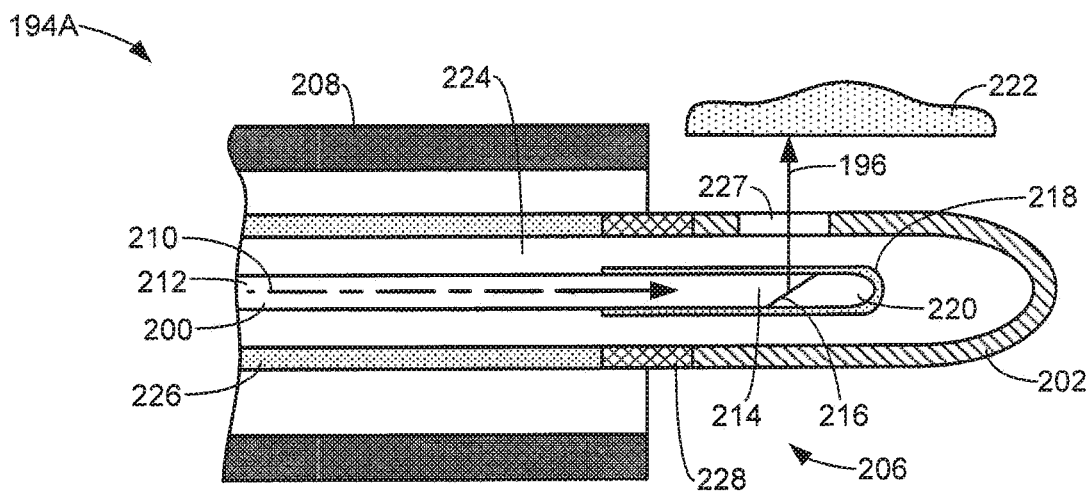
FIGS. 7 and 8 are simplified side cross-sectional views of a distal end of an exemplary energy delivery device in accordance with aspects of this disclosure respectively performing a laser operation and an electrical cauterization operation.
Figure 8:
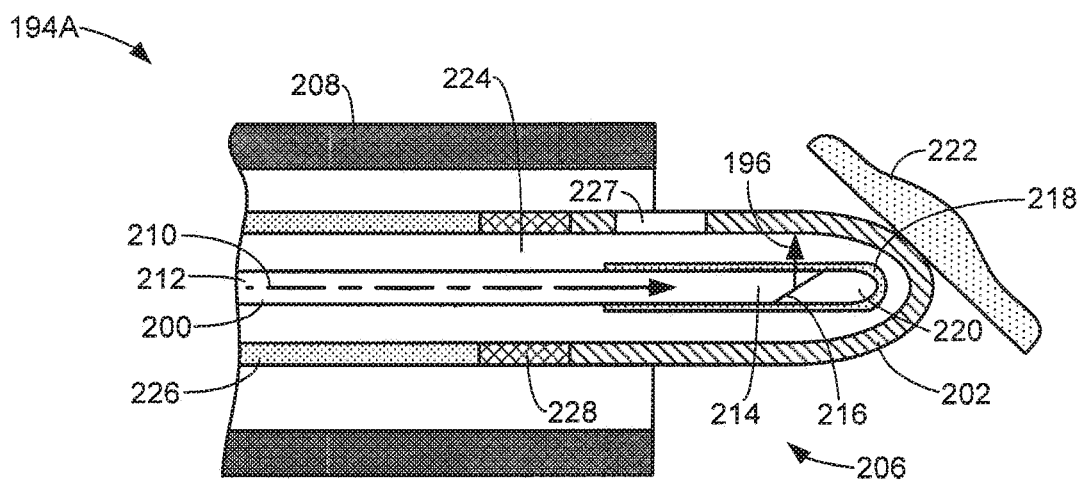

FIGS. 7 and 8 are simplified side cross-sectional views of a distal end 206 of an energy delivery device 194A in accordance with the aspects of this disclosure, respectively performing laser and cauterization operations. In some aspects, the energy delivery device 194A includes an endoscope 208, a distal end of which is shown in FIGS. 7 and 8. In some aspects, the endoscope 208 is used to deliver the laser fiber 200 and cauterization tip 202 to a desired treatment location to perform laser and cauterization operations on the patient.

As mentioned above, aspects of the laser fiber 200 include an end-fire configuration in which the laser energy 196 is discharged from the terminating end of the laser fiber 200 along the longitudinal axis 210 of the laser fiber 200. In some aspects, the laser fiber 200 is configured as a side-fire laser fiber, in which the laser energy 196 is discharged laterally with respect to the longitudinal axis 210, as shown in FIGS. 7 and 8. In some aspects, in order to discharge the laser energy 196 laterally, as depicted in FIGS. 7 and 8, the laser fiber 200 includes an optical fiber 212 having a terminating end 214 that includes a beveled surface 216. A fiber cap 218 covers the terminating end 214 and seals an air cavity 220 adjacent the beveled surface 216. This configuration causes the laser energy 196 transmitted through the optical fiber 212 to reflect off the beveled surface 216 laterally relative to the longitudinal axis 210 toward targeted tissue 222 to perform a laser operation on the tissue 222, as shown in FIG. 7. Such a laser fiber may also be used with other aspects described herein.

In some aspects, the energy delivery device 194A supports the laser fiber 200 within a lumen 224 of a member 226 that supports the cauterization tip 202. In some aspects, the cauterization tip 202 is formed of a thermally conductive material, such as metal, that is attached to the member 226. In some aspects, a thermally insulative portion 228 is positioned between the member 226 and the cauterization tip 202 to reduce the conduction of heat from the cauterization tip 202 to the member 226.

As can be seen in FIGS. 7 and 8, the cauterization tip 202 includes an opening or side port 227 therein to allow laser energy 196 to be discharged through the cauterization tip 202. During a laser treatment operation such as, for example, vaporization, the cauterization tip 202 is positioned over the laser fiber 200 such that the side port 227 aligns with the discharge path of the laser energy 196 as depicted in FIG. 7.

In some aspects, when cauterization is desired, a cauterization operation may be performed by moving the laser fiber 200 relative to the member 226 and the supported cauterization tip 202 to position the laser fiber 200 adjacent the cauterization tip 202, as shown in FIG. 8. That is, the laser fiber 200 is positioned within the member 226 and cauterization tip 202 such that the side port 227 no longer aligns with the discharge path of the laser energy 196 (FIG. 8). The laser source 192 is then activated to discharge the laser energy 196 to the cauterization tip 202. The cauterization tip 202 is heated in response to this exposure to the laser energy 196. The user of the energy delivery device 194 may then place the heated cauterization tip 202 in contact with the targeted tissue 222 to cauterize the tissue 222, as shown in FIG. 8.

Figure 9:
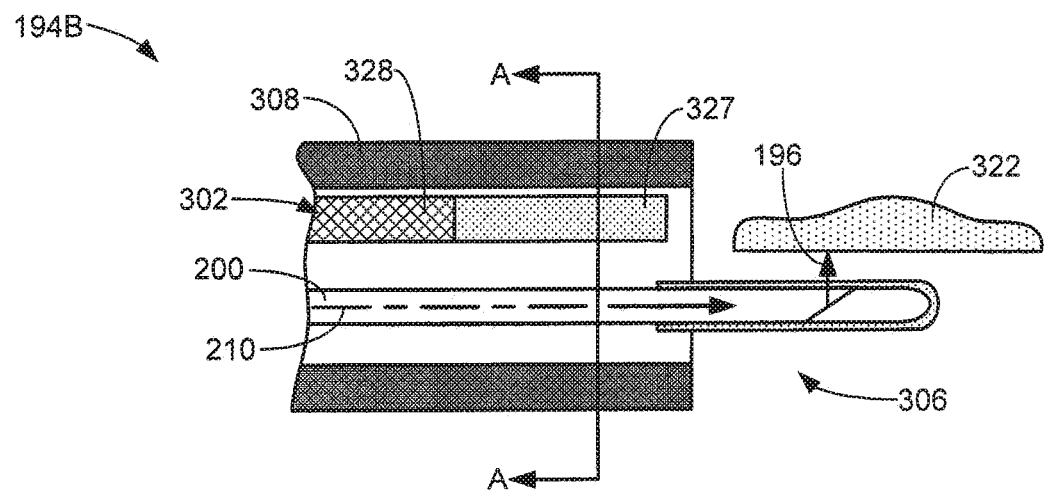
FIG. 9 is a simplified side cross-sectional view of a distal end of an exemplary energy delivery device performing a laser operation in accordance with aspects of this disclosure.
Figure 10:
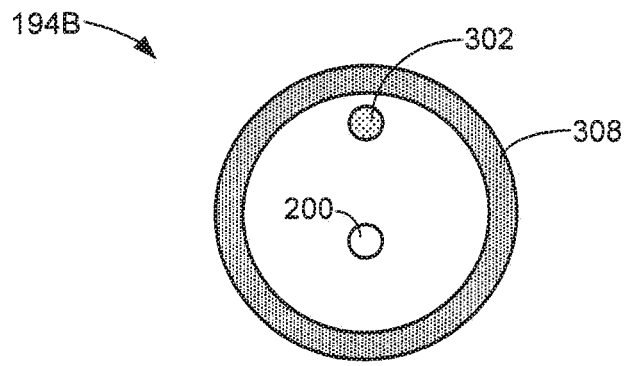
FIG. 10 is a front cross-sectional view of the exemplary energy delivery device of FIG. 9 taken generally along line A-A of FIG. 9.
Figure 11:
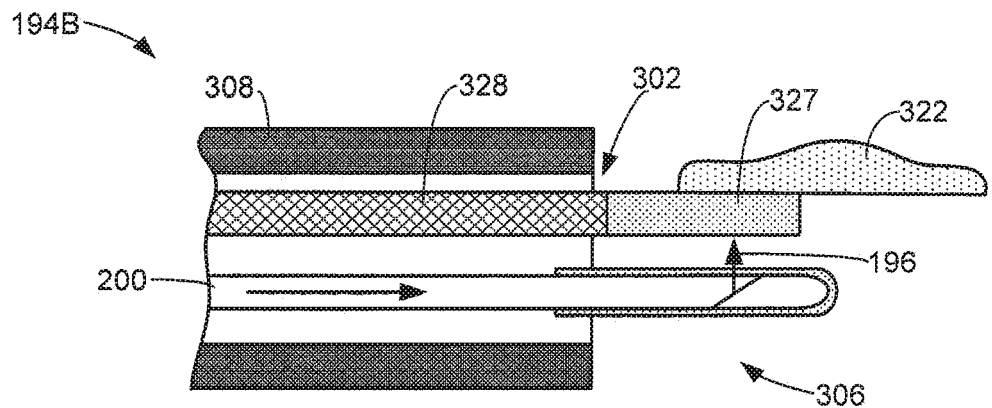
FIG. 11 is a simplified side cross-sectional view of the exemplary energy delivery device of FIG. 9 during a cauterization operation.

FIGS. 9-11 illustrate an energy delivery device 194B in accordance with additional exemplary aspects of this disclosure, which can be used with the system depicted in FIG. 6. For example, FIG. 9 is a simplified side cross-sectional view of the distal end 306 of an exemplary energy delivery device 194B performing a laser operation in accordance with aspects of this disclosure. As a further example, FIG. 10 is a front cross-sectional view of the exemplary energy delivery device 194B of FIG. 9 taken generally along the line A-A of FIG. 9. As yet another example, FIG. 11 is simplified side cross-sectional view of the exemplary energy delivery device 194B during a cauterization operation.

In some aspects, the energy delivery device 194B utilizes an endoscope 308 to support the laser fiber 200 and the cauterization member 302. The cauterization member 302 includes a thermally conductive portion 327 at its distal end. In some aspects, both the laser fiber 200 and cauterization member 302 are configured to move relative to each other and the endoscope 308, such as sliding by hand or other conventional techniques.

During a laser operation, the laser fiber 200 is extended through the distal end of the endoscope 308, as shown in FIG. 9. The laser source 192 (FIG. 6) is activated to deliver laser energy 196 through the laser fiber 200 and discharge the laser energy 196 to the targeted tissue 322. The laser operation (such as vaporization) is performed on the tissue 322 in response to the exposure to the laser energy 196. In some aspects, the cauterization member 302 is recessed within the endoscope 308 during the laser operation, as shown in FIG. 9.

In some aspects, the cauterization operation is performed by advancing the cauterization member 302 through the distal end of the endoscope 308, as shown in FIG. 11. In some aspects, the thermally conductive portion 327 of the cauterization member 302 is positioned adjacent the emission surface of the laser fiber 200 or discharge path of the laser energy 196. Thus, when the user activates the laser source 192, the laser energy 196 is transmitted through the laser fiber 200 and discharged into the thermally conductive portion 327 of the cauterization member 302. The thermally conductive portion 327 is heated in response to exposure to the laser energy 196. Cauterization is performed by placing the now heated conductive portion 327 in contact with the targeted tissue 322, as shown in FIG. 11. In some aspects, the cauterization member 302 includes a thermally insulative portion 328 that protects the endoscope 308 and/or portions of the laser fiber 200 from excessive heat generated during the cauterization operation.

Figure 12:
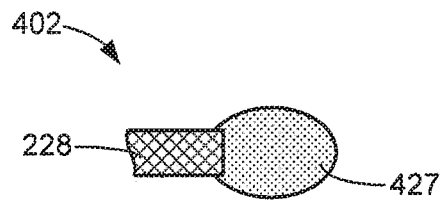
FIGS. 12 and 13 are simplified side cross-sectional views of exemplary heating tips in accordance with aspects of this disclosure.
Figure 13:
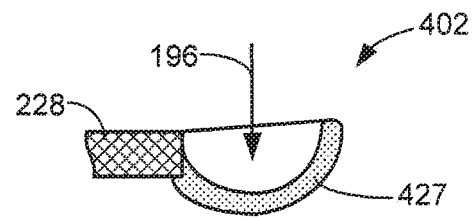

FIGS. 12 and 13 are simplified side cross-sectional views of exemplary cauterization members 402 in accordance with aspects of this disclosure. In some aspects, the thermally conductive portion 427 of the cauterization member 402 has a blunt shape, as shown in FIG. 12. In some aspects, the thermally conductive portion 427 has a concave shape, such as a half loop, in order to capture the laser energy 196, as shown in FIG. 13. The shape of the thermally conductive portion 427 can be any shape and can be selected based on the type of cauterization operation anticipated to be performed. The shape may affect the efficiency of the cauterization operation.

Figure 14:
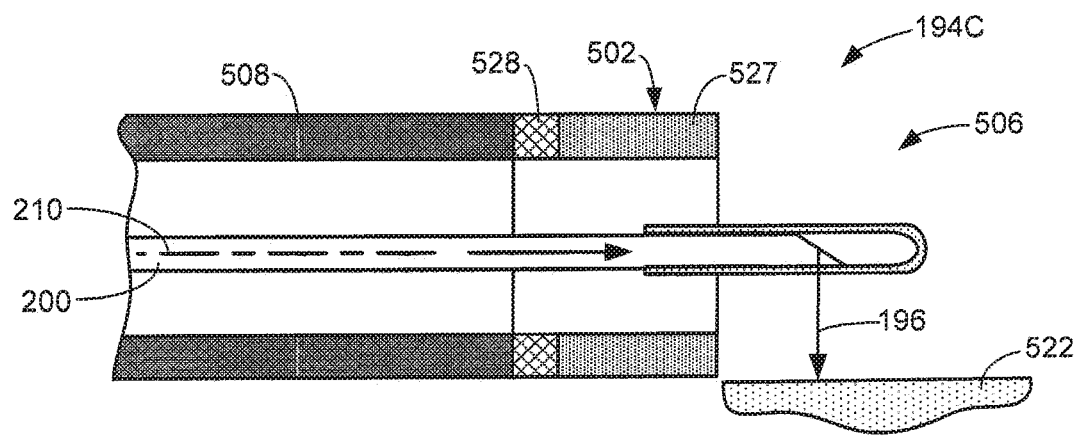
FIGS. 14 and 15 are simplified side cross-sectional views of an exemplary energy delivery device in accordance with aspects of this disclosure respectively performing laser and cauterization operations.
Figure 15:
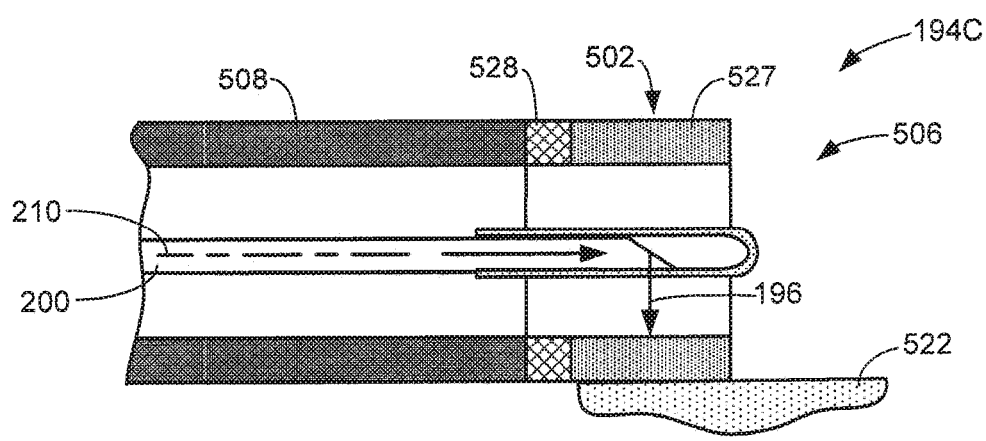

FIGS. 14 and 15 are simplified cross-sectional views of an exemplary energy delivery device 194C in accordance with aspects of this disclosure respectfully performing a laser operation and a cauterization operation. In some aspects, the cauterization member 502 is mounted to the distal end of the endoscope 508. In some aspects, the endoscope 508 is protected from the heat generated during the cauterization operation by insulating the endoscope 508 from the thermally conductive portion 527 with a thermally insulative portion 528.

During a laser operation, the laser fiber 200 is extended through the distal end 506 of the endoscope 508 and past the cauterization member 502 such that the laser energy 196 discharged from the laser fiber 200 is directed at the targeted tissue 522, as shown in FIG. 14.

To perform a cauterization operation, the laser fiber 200 is retracted into the endoscope 508 such that the laser energy 196 discharged from the laser fiber 200 is directed into the thermally conductive portion 527 of the cauterization member 502. The exposure of the thermally conductive portion 527 to the laser energy 196 heats the thermally conductive portion 527. The user can then place the heated thermally conductive portion 527 into contact with the targeted tissue 522 to perform cauterization on the tissue 522, as shown in FIG. 15. In some aspects, the cauterization member 502 is cylindrically shaped and surrounds the laser fiber 200. This simplifies the cauterization operation by ensuring that the thermally conductive portion 527 is exposed to the laser energy 196 when the laser fiber 200 is at a known position relative to the endoscope 508 regardless of the angular position of the laser fiber 202 about its longitudinal axis 210, as shown in FIG. 15.

In some aspects, the cauterization member 602 is in the form of an add-on device that can be removably attached to the distal end 506 of the endoscope 508. The attachment of the cauterization member 502 can be accomplished using any suitable technique. Thus, following a laser operation, the user can attach the cauterization member 502 to the endoscope 508 to perform a cauterization operation.

Figure 16:
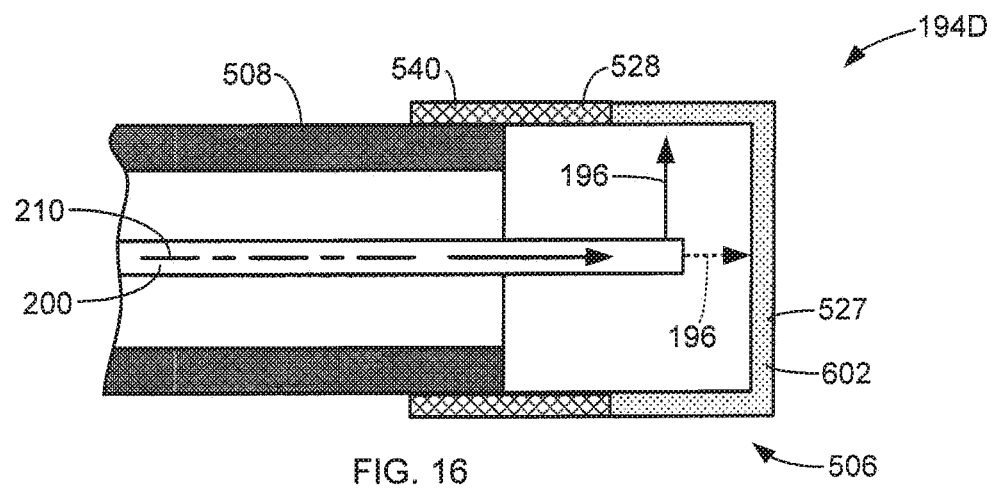
FIGS. 16 and 17 are simplified side cross-sectional views of exemplary energy delivery devices in accordance with aspects of this disclosure.
Figure 17:
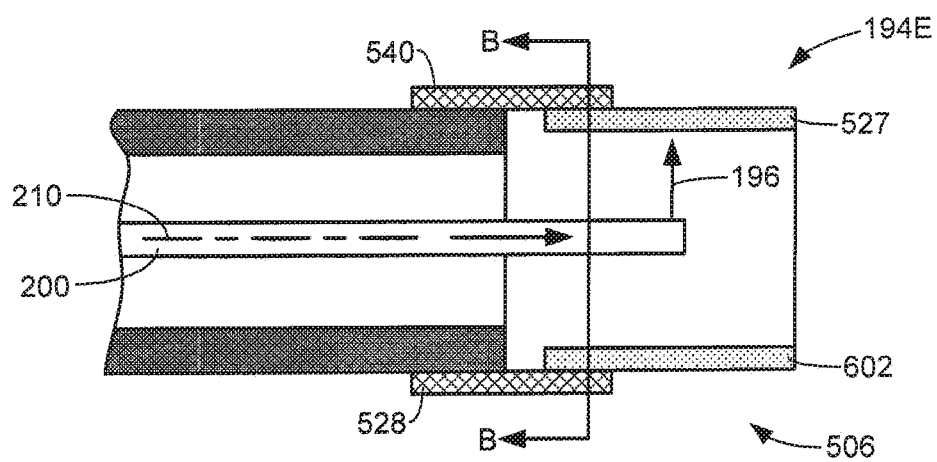

In some aspects, the cauterization member 502 includes a sleeve portion 540 that attaches to the distal end 506 of the endoscope 508, as shown in the simplified side cross-sectional views of exemplary energy delivery devices 194D and 194E shown in FIGS. 16 and 17. In some aspects, the sleeve portion 540 includes a thermally insulative portion 528 to prevent overheating of the endoscope 508. The sleeve portion 540 may be attached to the distal end of the endoscope 508 in many different ways. In some aspects, the sleeve portion 540 forms a socket that receives the distal end of the endoscope 508, as shown in FIGS. 16 and 17.

Figure 18:
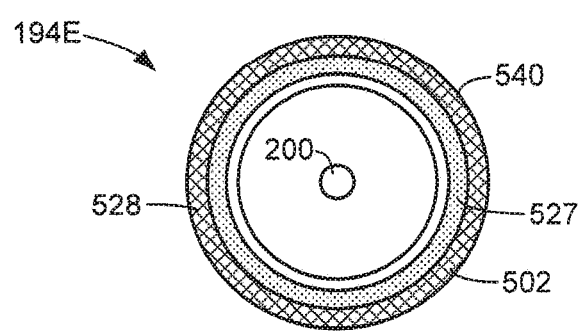
FIG. 18 is a front cross-sectional view of the exemplary energy delivery device of FIG. 17 taken generally along line B-B of FIG. 17.

In some aspects, the thermally conductive portion 527 of the cauterization member 502 covers the distal end of the laser fiber 200 and is configured to be exposed to laser energy 196 discharged along the longitudinal axis 210 of the laser fiber 200, as indicated by the phantom arrow 196 shown in FIG. 16. In some aspects, the distal end of the laser fiber 200 is configured to discharge laser energy 196 laterally with respect the longitudinal axis 210 of the laser fiber 200, as indicated in FIG. 17. In some aspects, the detachable cauterization member 502 has an open distal end, which allows laser operations to be performed by the laser fiber 200 by extending the laser fiber 200 beyond the open distal end of the cauterization member 502, as discussed above with respect to FIG. 14. In some aspects, the thermally conductive portion 527 surrounds the laser fiber 200, as shown in FIG. 18, which is a simplified front cross-sectional view of the energy delivery device 194E of FIG. 17 taken generally along line B-B.

In some aspects disclosed herein, it is important to monitor and control the temperature of the cauterization portion/tip/member of the energy delivery device in order to (1) prevent overheating of tissue, which can result in carbonization and (2) prevent damage to the cauterization portion/tip/member. Monitoring and measuring of the cauterization portion/tip/member can be achieved by detecting, collecting and/or analyzing the black body radiation or electromagnetic energy feedback produced at the cauterization portion/tip/member. This black body radiation or electromagnetic energy feedback can be used to control the laser power/energy to ensure that the cauterization portion/tip/member temperature remains at a safe level, for example, between 60-100 degrees Celsius, Methods and devices for detecting, collecting and/or analyzing the black body radiation or electromagnetic energy feedback produced at the cauterization portion/tip/member are described and disclosed in commonly-assigned International Patent Application No. PCT/US2014/61319, filed on Oct. 20, 2014, the entire contents of which are incorporated herein by reference in their entirety for all purposes.

In alternative aspects of the present disclosure, the cauterization portion/tip/member temperature can be controlled by a flowing irrigant. Irrigation flow can be achieved and controlled using the devices described and disclosed in commonly assigned U.S. Pat. Nos. 7,869,016 and 8,858,542, and commonly assigned U.S. patent application Ser. No. 14/471,945, filed on Aug. 28, 2014. The entire contents of U.S. Pat. Nos. 7,869,016 and 8,858,542, and U.S. patent application Ser. No. 14/471,945 are incorporated herein by reference in their entirety for all purposes. Additionally, irrigation can be provided to the cauterization portion/tip/member with an endoscope, cystoscope or other similar device.

Although the present disclosure has been described with reference to illustrative aspects for particular applications, the disclosure is not limited thereto. Those have ordinary skilled in the art and access to the teachings provided herein will recognize that additional modifications, applications, aspects, changes, and substitution of equivalents all fall in the scope of this disclosure, and may be made in form and detail without departing from the spirit and scope of this disclosure. Accordingly, the present disclosure is not to be considered as limited by the foregoing description.

What is claimed is:

1. A system comprising:
a cauterization device having a wall defining a lumen and a distal opening at a distal end of the cauterization device; and
an optical fiber configured to discharge laser energy, configured to move relative to the cauterization device, and configured to extend distally through the distal opening,
wherein the laser energy is configured to be discharged from the optical fiber towards a treatment area when the optical fiber is extended through the distal opening, and
wherein the laser energy is further configured to be discharged from the optical fiber towards the cauterization device.

2. The system of claim 1, further comprising:
an endoscope, wherein the cauterization device is at or adjacent to a distal end of the endoscope.

3. The system of claim 2, further including a thermally insulative portion between a portion of the endoscope and the cauterization device.

4. The system of claim 3, wherein the cauterization device is removably attached to the endoscope.

5. The system of claim 3, wherein the cauterization device extends proximally to a distalmost end of the thermally insulative portion.

6. The system of claim 3, wherein the thermally insulative portion includes a polymer or a ceramic.

7. The system of claim 1, wherein, when the optical fiber is in a first position parallel to the cauterization device, laser energy is discharged from the optical fiber towards the cauterization device to heat the cauterization device, and, when the optical fiber is extended through the distal opening at the distal end of the cauterization device, the laser energy is discharged towards the treatment area.

8. The system of claim 1, wherein the cauterization device includes a thermally insulative portion and a thermally conductive portion, and wherein the thermally conductive portion is provided distal to the thermally insulative portion.

9. The system of claim 1, further comprising a laser source, wherein the laser source is configured to discharge the laser energy from the optical fiber toward the treatment area at a first wavelength, and wherein the laser source is configured to discharge the laser energy from the optical fiber toward the cauterization device at a second wavelength different from the first wavelength.

10. A system comprising:
a cauterization device including a cauterization portion and a thermally insulative portion, wherein the cauterization portion is distal to the thermally insulative portion; and an optical fiber configured to (i) discharge laser energy, (ii) move relative to the cauterization device, and (iii) move between a first position and a second position;

wherein, in the first position, the optical fiber is configured to discharge the laser energy towards the cauterization portion, and wherein, in the second position, the optical fiber is outside of the cauterization device and is configured to discharge the laser energy outside of the cauterization device and toward a treatment area.

11. The system of claim 10, further comprising an endoscope, wherein the cauterization device is at or adjacent to a distal end of the endoscope.

12. The system of claim 10, wherein a distal end of the cauterization device includes an opening, and wherein the optical fiber extends distal to the opening in the second position.

13. The system of claim 10, wherein the thermally insulative portion includes a polymer or a ceramic.

14. The system of claim 10, further comprising a laser source, wherein the laser source is configured to discharge the laser energy from the optical fiber toward the treatment area at a first wavelength, and wherein the laser source is configured to discharge the laser energy from the optical fiber toward the cauterization portion at a second wavelength different from the first wavelength.

15. The system of claim 10, wherein discharging the laser energy to the cauterization portion causes the cauterization device to be heated.

16. The system of claim 10, wherein the second position, the optical fiber is configured to discharge the laser energy outside laterally relative to a longitudinal axis of the optical fiber.

17. A method comprising:
positioning a cauterization member adjacent a treatment area;
extending a laser fiber through an opening in a distal end of the cauterization member;
applying laser energy from the laser fiber to the treatment area or to tissue adjacent the treatment area;
retracting the laser fiber through the opening in the distal end of the cauterization member;
applying laser energy from the laser fiber to the cauterization member to heat the cauterization member; and
cauterizing tissue with the heated cauterization member.

18. The method of claim 17, wherein the laser energy applied to the treatment area or to the tissue adjacent the treatment area is at a first wavelength, and wherein the laser energy applied to the cauterization member is at a second wavelength, different from the first wavelength.

19. The method of claim 17, wherein the cauterization member is removably attached to an endoscope via a thermally insulative portion, and the cauterization portion is provided distal to the thermally insulative portion.

20. The method of claim 19, further comprising removing the cauterization member from the endoscope after the tissue at the treatment area is cauterized.

* * * * *